United States Patent

Wood et al.

[11] Patent Number: 5,408,029
[45] Date of Patent: Apr. 18, 1995

[54] AMINO ACID COPOLYMERS OF MALEIC ACID

[75] Inventors: Lousi L. Wood, Rockville; Gary J. Calton, Elkridge, both of Md.

[73] Assignee: SRCHEM, Inc., Elkridge, Md.

[21] Appl. No.: 132,288

[22] Filed: Oct. 6, 1993

[51] Int. Cl.$^6$ .................. C08G 69/10; C08G 63/91; C08G 69/48; C08G 73/00

[52] U.S. Cl. ........................... 528/328; 528/363; 528/367; 525/419; 525/420; 525/539; 525/540

[58] Field of Search ............ 528/328, 363, 367; 525/539, 540, 419, 420

[56] References Cited

U.S. PATENT DOCUMENTS

| | | | |
|---|---|---|---|
| 2,306,918 | 12/1942 | Weiss et al. | 528/345 |
| 3,052,655 | 9/1962 | Fox et al. | 528/313 |
| 3,846,380 | 11/1974 | Fujimoto et al. | 525/328.2 |
| 4,169,924 | 10/1979 | Barabas et al. | 525/377 |
| 4,363,797 | 12/1982 | Jacquet et al. | 424/70 |
| 4,534,881 | 8/1985 | Sikes et al. | 252/180 |
| 4,696,981 | 9/1987 | Harada et al. | 525/328.2 |
| 4,839,461 | 6/1989 | Boehmke | 528/363 |
| 4,996,292 | 2/1991 | Fox et al. | 582/328 |
| 5,057,597 | 10/1991 | Koskan | 528/328 |
| 5,064,563 | 11/1991 | Yamaguchi et al. | 252/174.23 |
| 5,219,952 | 6/1993 | Koskan et al. | 525/419 |

OTHER PUBLICATIONS

Harada et al. Copolyamino acids. Chem. Absts. vol. 104:207690m, Jun. 1986.

Dessaignes, Quart. Jour. Chem. Soc. of London, pp. 187-188, reprinted 1950, trans. Comp. Rendu. pp. 432-434, 1850, attached.

*Primary Examiner*—John Kight, III
*Assistant Examiner*—P. Hampton-Hightower
*Attorney, Agent, or Firm*—William S. Ramsey

[57] ABSTRACT

Polymers of maleic, fumaric or malic acids or maleic, fumaric or malic acid and ammonia with amino acids are prepared by heating at 180°-350° C., preferably 200°-300° C. The polymer formed may be converted to a salt by hydrolysis with a metal hydroxide or ammonium hydroxide.

15 Claims, No Drawings

AMINO ACID COPOLYMERS OF MALEIC ACID

FIELD OF THE INVENTION

This invention relates to a process for the production of polymers of maleic acid and ammonia with an amino acid.

BACKGROUND OF THE INVENTION

Economic methods of production of polymers of aspartic acid and its salts for use as inhibitors of corrosion of ferrous metals, fertilizers, tartar barrier agents, scale inhibition agents and dispersants such as those used for clays, ores, coal, pigments, soil or minerals in dishwashing and laundry detergents, and the like, are highly desirable. These polymers are particularly useful for the prevention of scale deposition in boiler water, reverse osmosis membranes and detergents and are readily biodegradable. Scale is composed to varying degrees of the sulfate, carbonate and phosphate salts of barium, calcium and strontium and magnesium hydroxide.

DESCRIPTION OF RELATED ART

A number of methods of preparation of peptide copolymers of aspartic acid are disclosed in the literature and other patents, however, due to limitations in the reaction conditions, their preparation has been uneconomic.

U.S. Pat. No. 3,846,380 discloses the preparation and composition of copolymers of polyamino acids by reacting a polyimide with primary or secondary aliphatic amines, followed by alkaline hydrolysis to provide surface active agents.

U.S. Pat. No. 4,696,981 discloses a method for making polyamino acids by microwaving amides, ammonium salts or monoamide-ammonium salts of malic acid, maleic acid or/and fumaric acid with one or more amino acids in ratios of 1:1 to 3:1 acid to amino acid with yields of 30–70%. It is further explained that upon heating, the ammonium salt of malic acid loses water to give a mixture of the amide of malic acid and/or the ammonium salt of maleic acid and/or its isomer, fumaric acid. Upon further loss of water, this salt is converted to the amide of maleic acid and/or fumaric acid, thus providing an equivalent starting point regardless of which of the acids, salts or mixtures thereof is used. Microwaves are said to be superior to the method of heating amino acids in a oil bath at 180° for four hours to achieve maximum yields as disclosed in Jpn. Kokai 60,203,636, Appl. 84/60,160 [C.A. 104, 207690m, 1986].

U.S. patent application Ser. No. 07/926,242, filed Aug. 7, 1992, by Louis L. Wood, incorporated herein by reference, discloses the preparation of copolymers of amino acids wherein polyamines, such as alkyl amines, are reacted with maleic acid and ammonia at temperatures of greater than 120° C. to form a polymer. These materials are excellent inhibitors of metal scale deposition.

U.S. Pat. No. 4,534,881 discloses the use of polyamino acids for the inhibition of the formation of $CaCO_3$.

SUMMARY OF THE INVENTION

Polymers were prepared by reacting maleamic acid; the amides, ammonium salts or monoamides of maleic acid, fumaric acid, or malic acid; or ammonia with maleic acid, fumaric acid, or malic acid or mixtures thereof; and an amino acid or mixture of amino acids, in a ratio of 3 parts acid to 1 part amino acid or greater, at temperatures greater than 180° C. for less than four hours. Hydrolysis of the polymer with a hydroxide provided a salt of the polymer having a high carboxylic acid content which is readily biodegradable. Although it is well known in the art that an equivalent of ammonia and maleic acid will form polysuccinimide and that hydrolysis of the polysuccinimide will provide polyaspartate, the formation of a polymer with less than an equivalent of ammonia is unexpected. The structure of the polymer differs in stoichiometry and is at present unknown. Although not wishing to be bound by any theory, the structures of maleic polymers prepared by catalysis of maleic anhydride by tributyl and triphenyl phosphine to form macro zwitterions provided succinic anhydride units and cyclopentanone derivatives or ketoolefinic units (H. Zweiful and T. Völker, Makromol. Chem., 170, 141–153, 1973). The products of the present invention differ from those made with one or more equivalents of ammonia, whether via aspartic acid, the amide of malic, maleic or fumaric acid, or with ammonia and malic, maleic or fumaric acid, by being lighter in color, having superior activity in one or more of the tests for usefulness and in being less expensive to prepare.

The interconversion of the starting materials, maleamic acid, the amides, ammonium salts or monoamide-ammonium salts of maleic acid, fumaric acid, or malic acid, and ammonia, by heating at low temperature is well known, see for example, U.S. Pat. No. 4,696,981, thus providing maleate monomers for the subsequent polymerization.

A polyamine containing amino acid provides a way of obtaining branching and cross-linking when thermal polymerization is used as opposed to methods of manufacturing polyamino acids via protecting group chemistries in which the amine alpha to the carboxylic acid is used exclusively which provides linear polymers.

The polymers of the present invention are useful as intermediates for reaction to provide surfactants, wet strength agents, warp sizing compounds, dispersants and the like. The salts of the polymers of this invention are useful for foaming agents, solubilizing agents, dispersing agents, emulsifying agents, rust-proofing agents, fiber-treating agents, level dyeing agents, retarding agents, detergent builders, detergent dispersants, water treatment agents, tartar control agents, inhibition agents for deposition of calcium, strontium and barium sulfate, carbonate and phosphate salts and salts of magnesium, super absorbent polymers, flocculants, coagulants, and the like.

One object of this invention is to provide a means of preparing copolymers of maleic acid and ammonia with amino acids. Yet another object of this invention is to provide novel compositions which are useful for the inhibition of scale deposition whether in water treatment, detergent addition, oral health care or cosmetic formulation. Still another object of is to provide compositions useful as dispersants. Yet another object of this invention is to provide novel compositions which may be further reacted to provide cosmetically useful compounds. Another object of this invention is to provide agents useful for the inhibition of tartar deposition when incorporated into a suitable dentifrice composition.

DETAILED DESCRIPTION OF THE EMBODIMENTS.

Copolymers of maleic acid may be obtained by reacting the mono- or diamides of maleic, fumaric or malic acids; or maleic, fumaric or malic acid and ammonia; with an amino acid or mixture of amino acids, at 180°–350° C., preferably 180°–300°C., for less than four hours. The polymer may be converted polymer having a high carboxylic acid content by hydrolysis with a metal hydroxide or ammonium hydroxide.

The acid or amide is mixed with the amino acid, or mixture thereof, in an aqueous medium, followed by the addition of the desired amount of ammonia in the form of gaseous ammonia or as its aqueous solution. This mixture is then heated to remove water. As water is removed, the mixture becomes a solid and then a melt of the mixture is formed. Water removal continues as the reaction proceeds and the temperature is brought to 120°–350° C. When the copolymer has come to a constant weight, which, depending on the temperature, may occur in less than 2 minutes, the reaction mixture is allowed to cool. Typically, the reaction may take up to 4 hours at 180°C., whereas it may take less than 3 minutes at 300°C. The copolymer formed can be used to make other novel and useful products by reactions such as those described in U.S. Pat. No. 4,363,797, wherein useful derivatives for cosmetic use are described or can be hydrolyzed with metal hydroxides or ammonium hydroxide to provide the appropriate salt of polyaspartic acid. The hydroxides useful in hydrolyzing the copolymers include the alkali and alkaline earth metal hydroxides and ammonium hydroxide, and other metal hydroxides, examples of which as their cations are $Na^+$, $K^+$, $Mg^+$, $Li^+$, $Ca^{++}$, $Zn^{++}$, $Ba^{++}$, $Co^+$, $Fe^{++}$, $Fe^{++}$, and $NH^+_4$. Solutions of the salts of the copolymers formed in this manner have excellent scale inhibition performance, dispersion characteristics and molecular weight range. The addition of quantities of a polyamine containing amino acid, e.g., lysine or arginine, provides higher molecular weights and non-linearity. As opposed to commonly synthesized or natural linear peptides, the introduction of a second amine in the thermal reaction provides a branch point, giving different compositions and properties. These copolymers form gels at high levels of the polyamine containing amino acid, which are capable of absorbing large quantities of water. Further manipulation to remove the water or the salts can be carried out to provide water free powders of the salts or the free acid.

Any amino acid may be used to produce these copolymers. Examples of suitable polyamine containing amino acids include lysine, histidine and arginine. Other useful amino acids are alanine, valine, leucine, isoleucine, proline, phenylalanine, tryptophan, methionine, glycine, serine, threonine, taurine, cysteine, tyrosine, asparagine, glutamine, aspartic acid and glutamic acid. These lists are not exhaustive, but are used by way of example only.

These polymers are useful as inhibitors of corrosion of ferrous metals, fertilizers, tartar barrier agents, scale inhibition agents, such as those used in prevention of scale deposition in boiler water, reverse osmosis membranes and detergents, and dispersants such as those used for clays, ores, coal, pigments, soil or minerals in dishwashing and laundry detergents, and the like.

The copolymers provided by the present invention are advantageous for inhibition of scale deposition, especially where an increased molecular weight is desirable to provide appropriate biodegradability and retention on surfaces for preventing salt deposition whether in water treatment, as a detergent additive, or as an ingredient in oral health care or cosmetic formulations. The copolymers are excellent dispersants and may be used to disperse pigments, clays, ores, coal slurries, and the like or in formulations of detergents to suspend soil and mineral particles.

EXAMPLE 1

Copolymer from monoammonium maleate and lysine

A solution of 4.6 g (0.025 mol) lysine HCl in 10 ml of water was mixed with 2.0 g of 50% NaOH in $H_2O$ (0.025 mol NaOH). To this solution was added 10 g (0.1 mol) maleic anhydride. The mixture was stirred several minutes. After stirring for 10 min, the slurry was mixed with 30 g water and 29.1 g maleic anhydride. Upon stirring 15 min, the maleic anhydride dissolved to give a white slurry to which was added 47 g 30% $NH_4OH$ in $H_2O$ to give a clear colorless solution.

Water was removed at a bath temperature of 190°–210° C. for 8 min resulting in a pink-tan foam. The foam was cooled and pulverized and the resultant powder was tumbled at 200°–235° C. for 9 min to again give a pink-tan foam. Finally the foam was again pulverized and then tumbled at 230°–240° C. for 11 min to give 42.4 g of pink tan powder (theory for a copolymer of maleic acid, ammonia and lysine is 44.4 g).

The solids were slurried in 60 g of water and dissolved with 16 g NaOH in 24 g of water to give a clear red-brown solution of the sodium salt of a copolymer of lysine, ammonia and maleic acid. After adding 5.5 g of 30% $H_2O_2$ in water and stirring for 8 hr at 25° C., the solution was a clear yellow and contained 40% active solids, pH 11.0.

Gel permeation chromatography (GPC) on a 1 cm × 18 cm, Sephadex G-50 (a product of Pharmacia, Piscataway, N.J.) column in a mobile phase of 0.02M sodium phosphate buffer, pH 7.0, running at 0.5 ml/min, with detection in the UV at 240 nm gave a peak centered at 14.0 min.

Inhibition of calcium carbonate precipitation by the calcium drift assay is measured by forming a supersaturated solution of calcium carbonate by adding 29.1 ml of 0.55M NaCl and 0.01M KCl to 0.3 ml of 1.0M $CaCl_2$, 5 microliter of sample (100 mg of the solids in 10 ml of water) and 0.6 ml of 0.5M $NaHCO_3$. The reaction is initiated by adjusting the pH to 8.55–8.65 by titration with 0.5N NaOH. At three minutes, 10 mg of $CaCO_3$ is added to initiate the reaction and the pH is recorded. The decrease in pH is directly correlated to the amount of $CaCO_3$ that precipitates. The additive concentration in the final test solution is 1.7 ppm.

A comparison of the material of this example and other materials (all at 1.7 ppm) in the $CaCO_3$ drift test at 20 min and their relative GPC times is given below.

TABLE 1

|  | drift in pH | GPC (min) |
|---|---|---|
| blank | 1.11 |  |
| 5000 mw polyacrylate | 0.20 |  |
| maleic acid/ammonia homopolymer | 0.39 | 22 |
| aspartic acid homopolymer | 0.43 | 18.5 |
| maleic acid/alanine copolymer | 0.45 | 24.5 |
| maleic acid/hexamethylenediamine copolymer | 0.93 | 12.5 |
| maleic acid/lysine copolymer | 0.63 | 14.0 |

EXAMPLE 2

Preparation of a maleic polymer gel with an amino acid and ammonia

To a solution of 11 g (0.06 moles) of lysine in 40 g of water containing 4.8 g of NaOH was added 33.3 g (0.34 moles) of maleic anhydride while stirring at 70°–75° C. for 10 min to give a slurry of maleic acid. To this slurry was added 23 g of 25% aqueous ammonium hydroxide (0.34 moles $NH_3$) with stirring and cooling. This solution was then heated with the results in Table 2.

TABLE 2

| Time period | Time (min) | Temperature °C. | weight (g) |
|---|---|---|---|
| 1 | 10 | 185–195 | 51.5 |
| 2 | 10 | 200–225 | 48.9 |
| 3 | 10 | 200–235 | 46.6 |
| 4 | 10 | 220–235 | 45.5 |
| 5 | 10 | 220–235 | 45.2 |

A portion of the powder from period 5 was dissolved in a aqueous NaOH to give insoluble gel particles retaining 20 times their weight in water.

EXAMPLE 3

Preparation of a maleic polymer with an amino acid and less than 1 equivalent of ammonia To a solution of 4.6 g (0.025 moles) of lysine in 40 g of water containing 1.0 g of NaOH was added 39.2 g (0.4 moles) of maleic anhydride while stirring at 70°–75° C. for 10 min to give a pale yellow slurry of maleic acid. To this slurry was added 5.0 g (0.29 moles) of anhydrous ammonia with stirring and cooling. This solution was then treated with heat as in Example 1 to give 44.0 g of pink-tan powder which was insoluble in water.

The powder was dissolved in a solution of 9.0 g of water containing 1.3 g of NaOH to give a clear red-brown solution, estimated to contain 36% solids. The GPC of this solution as in Example 1 gave a peak centered at 13 min.

EXAMPLE 4

Preparation of a maleic polymer with an mono-amine containing amino acid and ammonia Maleic anhydride, 19.5 g (0.2 moles), was added to 40 ml of water, followed by the addition of 12 g of 30% aqueous ammonium hydroxide (0.2 moles $NH_3$) and 2.0 (0.022 moles) of L-alanine. The solution was tumbled at 190°–210° C. for 10 min, pulverized and tumbled at 235°–245°C. for ten min. The resulting foam was again pulverized and tumbled another 10 min at 235°–245°C. to give 21.3 g of a brown powder. The powder was slurried in 40 g of water and dissolved with 7.6 g NaOH in 12 ml of water to give a clear red-brown solution containing 36% solids.

The GPC of this solution as in Example 1 gave a peak centered at 24 min. Inhibition of calcium carbonate precipitation as measured by the calcium drift assay of Example 1, gave a change in pH of 0.45, whereas the blank was 1.1.

To assay for the inhibition of $CaSO_4$, the material to be tested as an inhibitor of calcium sulfate scale formation was added at the level given below to a solution of 10 ml of calcium chloride solutions 17.3 g of $CaCl_2$ dihydrate in 800 g of water containing 33 g of NaCl). To this solution was then added 10 ml of sulfate solution (16.8 g of $Na_2SO_4$ and 33 g NaCl in 800 ml of water). The mixture was then sealed and maintained at 65° C. for 16 hours. Finally the mixture was filtered through Whatman #2 paper and dried at 65° C. for 8 hours, after which the weight of precipitate was determined. At 2.5 ppm the polymer of this example gave a precipitate of 3.0 mg whereas the blank was 84 mg.

Dispersant activity was determined by examining kaolin clay dispersions. Kaolin dispersion was run by placing the sample in a 12×100 mm test tube containing 5 ml of deionized water and adding 40,000 ppm kaolin clay. The height of the suspended solids was measured and compared to a control in which no dispersant had been added. A higher value indicates better dispersancy. The polymer of this example gave a height of 48 mm of dispersed solids, whereas the control gave a height of 0 mm of dispersed solids.

EXAMPLE 5

Preparation of a maleic polymer with a polycarboxylic acid containing amino acid and ammonia To a solution of 19.5 g (0.2 moles) of maleic anhydride while stirring at 70°–25° C. for 45 min to give a slurry of maleic acid. To this slurry was added 12 g of 30% aqueous ammonium hydroxide (0.2 moles $NH_3$) and 2.0 g of glutamic acid (0.014 moles). The solution was tumbled at 190°–210° C. for 10 min, pulverized and tumbled at 235°–245° C. for ten min. The resulting foam was again pulverized and tumbled another 10 min at 235°–245° C. to give 21.3 g of a brown powder. The powder was slurried in 40 g of water and dissolved with 7.6 g NaOH in 12 ml of water to give a clear red-brown solution containing 36% solids.

Inhibition of calcium carbonate precipitation as measured by the calcium drift assay of Example 1, gave a change in pH of 0.55, whereas the blank was 1.1. In the $CaSO_4$ precipitation assay of Example 4, the polymer of this example at 2.5 ppm gave a precipitate of 9.0 mg whereas the blank was 84 mg. In the kaolin clay dispersion assay of Example 4, the polymer of this example gave a height of 47 mm of dispersed solids, whereas the control gave a height of 0 mm of dispersed solids.

EXAMPLE 6

Copolymer from monoammonium maleate and high levels of lysine

A solution of 6.9 g (0.038 mole) lysine HCl in 15 ml of water was mixed with 1.5 g of NaOH in $H_2O$. To this solution was added 39.2 g (0.4 mol) maleic anhydride. Upon stirring 15 min, the maleic anhydride dissolved to give a white slurry to which was added 24 g $NH_4$ to give a clear colorless solution.

The slurry was heated, cooled and pulverized for four successive 10 min heating period yielding 44.8 g of red-tan powder. A 4.6 g portion of the powder was slurried in 19 g of water containing 0.4 g NaOH to give a clear red-brown extremely viscous syrup.

It will be apparent to those skilled in the art that the examples and embodiments described herein are by way of illustration and not of limitation, and that other examples may be utilized without departing from the spirit and scope of the present invention, as set forth in the appended claims.

We claim:

1. A process for the preparation of a polymer comprising heating a compound selected from the group consisting of
    1) ammonia with a member selected from the group consisting of malic, maleic and fumaric acids and 2) maleamic acid, the monoamide or diamide of malic, maleic and fumaric acids;

with an amino acid or mixture of amino acids, at temperatures above 180° C. for less than four hours.

2. The process of claim 1 wherein the amino acid is selected from a group consisting of lysine, histidine, arginine, alanine, valine, leucine, isoleucine, proline, phenylalanine, tryptophan, methionine, glycine, serine, threonine, taurine, cysteine, tyrosine, asparagine, glutamine, aspartic acid and glutamic acid.

3. The process of claim 1 wherein the amino acid is lysine.

4. The process of claim 1 wherein the amino acid is alanine.

5. The process of claim 1 wherein the member is maleic acid.

6. The process of claim 1 wherein the resultant polymer is converted into a salt by adding an alkaline-earth or alkali metal hydroxide or ammonium hydroxide.

7. A polymer produced by thermally polymerizing (1) a member of the group consisting of maleic acid, malic acid and fumaric acid, (2) ammonia, and (3) an amino acid in which the ratio of said acid to amino acid is greater than 3:1 at temperature above 180° C. for less than four hours.

8. The polymer of claim 7 which is converted to a salt by the addition of an alkaline-earth or alkali metal hydroxide or ammonium hydroxide.

9. The polymer of claim 7 wherein the amino acid is lysine.

10. The polymer of claim 7 wherein the amino acid is arginine.

11. The polymer of claim 7 wherein the amino acid is selected from the group consisting of lysine, histidine, arginine, alanine, valine, leucine, isoleucine, proline, phenylalanine, tryptophan, methionine, glycine, serine, threonine, taurine, cysteine, tyrosine, asparagine, glutamine, aspartic acid, and glutamic acid.

12. The polymer of claim 7 wherein the amino acid is lysine.

13. The polymer of claim 7 wherein the amino acid is alanine.

14. The polymer of claim 7 wherein the member of the group consisting of maleic acid, malic acid and fumaric acid is maleic acid.

15. The polymer of claim 7 wherein the resultant polymer is converted into a salt by adding an alkaline-earth hydroxide or alkali metal hydroxide or ammonium hydroxide.

* * * * *